United States Patent [19]

Inoue et al.

[11] 4,112,218

[45] Sep. 5, 1978

[54] METHOD OF PREPARING STEROL GLYCOSIDES FROM PLANTS

[75] Inventors: Sho Inoue; Akira Sano, both of Uji; Koji Kitaguchi, Joyo, all of Japan

[73] Assignee: Nippon Shinyaku Co., Ltd., Japan

[21] Appl. No.: 746,940

[22] Filed: Dec. 2, 1976

[30] Foreign Application Priority Data

Aug. 31, 1976 [JP] Japan .................................. 51-104656

[51] Int. Cl.$^2$ ............................................. C07J 17/00
[52] U.S. Cl. ........................................ 536/5; 424/182; 536/6; 536/7
[58] Field of Search ...................................... 536/5, 6, 7

[56] References Cited

U.S. PATENT DOCUMENTS

| | | | |
|---|---|---|---|
| 2,306,547 | 12/1942 | Langlois .................... | 536/5 |
| 2,691,011 | 10/1954 | Perlman et al. ............ | 536/5 |
| 2,746,957 | 5/1956 | Perlman et al. ............ | 536/5 |

FOREIGN PATENT DOCUMENTS

| | | | |
|---|---|---|---|
| 484,578 | 7/1952 | Canada ........................ | 536/5 |
| 728,961 | 4/1955 | United Kingdom ........ | 536/5 |

*Primary Examiner*—Johnnie R. Brown
*Attorney, Agent, or Firm*—Jacobs & Jacobs

[57] ABSTRACT

Sterol glycosides are isolated from sterol glycoside-containing plant material by heating the material in alkaline lower alkanol at elevated temperatures in the presence of an alkali metal carbonate, bicarbonate or nitrate to effect formation and precipitation of a complex which is then isolated.

7 Claims, No Drawings

METHOD OF PREPARING STEROL GLYCOSIDES FROM PLANTS

DETAILED DESCRIPTION OF THE INVENTION

The present invention is related to a novel method of preparing sterol glycosides from plants.

It is known that the sterol glycosides are widely distributed in the world of plants together with the esters in which fatty acid is bonded to the 6-position of the sugar. Sterol glycosides are usually composed of glucose in which two or more sterols are being mixed depending upon the kind of plants. Representative examples may be campesterol, stigmasterol, β-sitosterol, etc.

These sterol glycosides obtained from the plants are effective for use as styptics and blood-vessel reinforcing agents.

The content of sterol glycosides is usually less than 0.04% with respect to the weight of the dried plants. But the oil foots or gums obtained in industrially manufacturing the plant oils contain sterol glycosides in large concentration. For example, crude lecithin of soy beans contains sterol glycosides in an amount of more than 3%, and is therefore a very useful raw material for the manufacture of sterol glycosides.

The sterol glycosides can be obtained from the oil foots (gum) by a method in which the crude lecithin of soy beans is treated and purified successively using organic solvents such as acetone, methanol, ether, pyridine, etc., or by a method by which the oil foots are decomposed with a potassium hydroxide in methanol, and separated and purified by column chromatography. However, these methods do not provide large amounts of sterol glycosides efficiently and economically. These methods require clumsy operation and various sorts of organic solvents, and are not suited for preparing sterol glycosides in large amounts.

Therefore, in an attempt to obtain the sterol glycosides in large amounts from the oil foots by simple operation, in good yields and economically, the inventors of the present invention have conducted extensive study concerning the method in which the oil foots (gum) is heated and decomposed in small amount of methanol by a customary manner, and the sterol glycosides dissolved therein are directly precipitated selectively and in high yields.

As a result, the inventors have found a remarkable precipitation reaction created by the sterol glycosides, carbonates such as potassium carbonate, sodium carbonate, potassium bicarbonate, sodium bicarbonate and lithium carbonate, and inorganic salts such as potassium nitrate, in an organic solvent.

The above precipitation reaction is very selective the sterol glycosides. The sterol glycosides are selectively and completely precipitated with heating if, for example, potassium carbonate is dissolved with heating in highly concentrated alkaline alcohol decomposition liquid of oil foots (gum) which may contain large amounts of fatty acid salts and other impurities.

In general, according to the method of the present invention of preparing the sterol glycosides from the oil foots, the oil foots is heated and decomposed in methanol of an amount of 3 to 4 times of said oil foots by weight in the presence of an alkali to remove impurities, and to which is added, for example, a potassium carbonate followed by heating for several hours. The combined product of sterol glycosides and potassium carbonate is then selectively and completely precipitated while the solution is still hot. The potassium carbonate present in the precipitated sterol glycosides is then easily dissolved and removed by washing with water or washing with methanol which contains acetic acid in small amounts.

The sterol glycosides obtained by the abovementioned simple processing contain minor amounts of impurities and feature very high purity. For instance, the purity of sterol glycosides obtained from the soy bean lecithin reaches 98% or higher. As required, the thus obtained crude crystals can be further refined easily through a single recrystallization using a generally employed organic solvent such as alcohols, dioxane or pyridine.

Examples of the organic solvents for use in the present invention are lower alcohols such as methanol, ethanol and propanol. From the standpoint of economy and solubility for the carbonates, it is most desirable to use methanol. The solvent used can be recovered and put into reuse immediately.

As mentioned in detail in the foregoing, the present invention makes it possible to prepare the sterol glycosides of high purity in large amounts and economically through such a simple operation that is not found in the prior arts, reliably and within short periods of time.

Below are illustrated concrete Examples of preparing the sterol glycosides from the soy bean lecithin sold in the market.

EXAMPLE 1

10 Kg of a commercially available soy bean lecithin was admixed with 40 l of methanol in which is dissolved 1.6 Kg of potassium hydroxide. The mixture was heated and stirred at boiling temperature for 3 hours, and the impurities were removed while the mixture was still hot. To the mixture was added 0.5 Kg of anhydrous potassium carbonate, and the resulting mixture was heated and stirred at boiling point for another 5 hours. The precipitated crystals were separated by filtration together with potassium carbonate while the mixture was still hot, washed with small amounts of methanol to remove the adhering reaction liquid. The product was then washed with water sufficiently to remove potassium carbonate, and dried to obtain 315 g of crude crystals. The crude crystals were recrystallized from 10 l of dioxane to obtain 300 g of the purified sterol glycosides, yield 3.0%, melting point 274° C to decomposition. A thin layer chromatography (silica gel) showed a single spot at $R_f$ 0.4 (benzene: ethanol = 5:1).

Element analysis (calculated as $C_{35}H_{60}O_6$):
Calculated: C 72.85 H 10.49
Found: C 72.26 H 10.29.

EXAMPLE 2

100 Kg of a commercially available soy bean lecithin was admixed with 500 l of methanol in which has been dissolved 16 Kg of potassium hydroxide. The mixture was heated and stirred at boiling point for 3 hours, and the impurities were removed while the mixture was still hot. To the mixture was added 5 Kg of sodium hydrogen carbonate, and the resulting mixture was heated and stirred at boiling temperature for another 5 hours. The precipitated crystals were separated by filtration together with sodium hydrogen carbonate while the mixture was hot, washed with a small amount of methanol to remove the adhering reaction liquid. The product was then washed with water sufficiently to remove sodium hydrogen carbonate, and dried to obtain 3.1 Kg of crude crystals. The crude crystals were recrystallized from 100 l of dioxane to obtain 3.0 Kg of refined sterol glycosides, yield 3.0%, melting point 274° C to decomposition. A thin layer chromatography (silica gel) showed a single spot at $R_f 0.4$ (benzene: ethanol = 5:1).

Element analysis: C 72.14 H 10.29.

The hemostatic effect of steryl-$\beta$-D-glucoside (SG) prepared by the present invention method can be observed in the Motohashi et al. model [Tokyo Jikeikai Medical College Bulletin 75 (5) 1959] by sharply amputating 1 cm-long tail tip of each of the mice divided in groups of ten and measuring the time which elapsed until threadlike bleeding from the amputated tail end in water is completely stopped. The results, together with analogous results for known hemostatic agents, can be summarized as follows:

Table 1

| Compound | $ED_{50}$ (mg/kg) | | |
|---|---|---|---|
| | i.v. | i.p. | p.o. |
| SG | 0.082 | 0.110 | 1.66 |
| Carbazochrome sodium sulfonate (Adona AC-17) | 3.6 | 5.4 | 36.0 |
| Conjugated estrogen (Premalin) | 14.5 | — | — |

As is apparent from the above, SG was approximately 45 times as effective on i.v. and i.p. administrations and approximately 22 times as effective on p.o. administration as the control drug carbazochrome sodium sulfonate and about 177 times as effective on i.v. administration as conjugated estrogen (ref. lit.: Wallner et al. Med. Klin. 66 1413, 1971).

The surprising vascular stabilizing effect of the compound SG can also be shown in a number of recognized models of which the following are typical.

The degree of pulmonary hemorrhage in mice under reduced pressure of 50 ±0.5 mm Hg/15 sec was assessed by the scoring method, the $ED_{50}$ of SG being calculated from the ratio of inhibiting rate for treated animals over that for the control group according to the method of G. J. Mojovski et al., J. Pharmacol. Exp. Therap. 80, 1, 1944.

Table 2

| Compound | $ED_{50}$ (mg/kg) | | |
|---|---|---|---|
| | i.v. | i.p. | p.o. |
| SG | 2.00 | 1.70 | 58.0 |
| Carbazochrome sodium sulfonate | 80.0 | 112.0 | 400.0 |
| Conjugated estrogen | — | 100.0 | — |

SG was more than 40 times more effective on i.v. administration, approximately 55 times more effective on i.p. administration and more than 7 times more effective on p.o. administration than carbazochrome sodium sulfonate and more than 50 times more effective on i.p. administration than conjugated estrogen.

What is claimed is:

1. Process for the isolation of sterol glycosides from sterol glycoside-containing plant material which comprises heating said material in alkaline lower alkanol at temperatures up to the boiling point of said alkanol together with an alkali metal salt selected from the group consisting of carbonate, bicarbonate and nitrate, separating the solid which forms and removing the alkali metal salt and any other inorganics from said solid by washing with water.

2. Process according to claim 1 wherein said sterol glycoside includes at least one of campesterol, stigmasterol and $\beta$-sitosterol.

3. Process according to claim 1 wherein said plant material is soy bean lecithin which has been treated with base.

4. Process according to claim 1 wherein said alkali metal salt is a sodium or potassium carbonate or bicarbonate.

5. Process according to claim 1 wherein sodium bicarbonate is used.

6. Process according to claim 1 wherein said lower alkanol is methanol.

7. Process according to claim 1 wherein soy bean lecithin is heated with alkaline methanol at reflux temperatures, insoluble impurities are removed from the hot solution by filtration, said methanol solution is heated with potassium carbonate, sodium carbonate, sodium bicarbonate or potassium bicarbonate, and the solid which forms is separated by filtration and washed with water.

* * * * *